(12) United States Patent
Ingalhalikar et al.

(10) Patent No.: US 11,389,203 B2
(45) Date of Patent: Jul. 19, 2022

(54) SEAL-LESS SELF-ACTUATING GROWING ROD SYSTEMS

(71) Applicant: Indius Medical Technologies Private Limited, Maharashtra (IN)

(72) Inventors: Aditya Ingalhalikar, Maharashtra (IN); Sagar Sathaye, Maharashtra (IN); Manali Kunte, Maharashtra (IN)

(73) Assignee: INDIUS MEDICAL TECHNOLOGIES PRIVATE LIMITED, Maharashtra (IN)

( * ) Notice: Subject to any disclaimer, the term of this patent is extended or adjusted under 35 U.S.C. 154(b) by 0 days.

(21) Appl. No.: 17/237,660

(22) Filed: Apr. 22, 2021

(65) Prior Publication Data

US 2021/0330361 A1    Oct. 28, 2021

(30) Foreign Application Priority Data

Apr. 23, 2020   (IN) .............................. 202021017386

(51) Int. Cl.
*A61B 17/70*   (2006.01)
*A61B 17/00*   (2006.01)

(52) U.S. Cl.
CPC ... *A61B 17/7017* (2013.01); *A61B 2017/00539* (2013.01)

(58) Field of Classification Search
CPC ............ A61B 17/7014; A61B 17/7017; A61B 17/7019; A61B 17/7025; A61B 2017/00535; A61B 2017/00539
See application file for complete search history.

(56) References Cited

U.S. PATENT DOCUMENTS

2016/0106471 A1*  4/2016  Lynch .................. A61B 17/702
                                                                     606/258

* cited by examiner

*Primary Examiner* — Eduardo C Robert
*Assistant Examiner* — Christina Negrellirodriguez
(74) *Attorney, Agent, or Firm* — Foley & Lardner LLP

(57) ABSTRACT

The present disclosure relates to a dynamic-seal-less self-actuating growing rod system (100) comprising at least one cylindrical static rod (2), at least one piston rod (6), coaxially coupled with said static rod (2) and configured to distract longitudinally out of the static rod (2); at least one fluid source (8) holding at least one sterile biocompatible fluid at a pre-determined pressure; at least one fluid transfer port (10) configured to transfer said sterile biocompatible fluid in said fluid source (8) to at least one fluid receptacle (12) at the same pre-determined pressure, wherein said at least one fluid receptacle (12) is in contact with said second piston end (6b) of said piston rod (6) at a first receptacle end (12a) and is connected to said fluid transfer port (10) at a second receptacle end (12b).

12 Claims, 8 Drawing Sheets

SEAL-LESS SELF-ACTUATING GROWING ROD SYSTEMS

The present application takes priority from the previously filed Indian Provisional application number 202021017386 titled "SEAL-LESS SELF-ACTUATING GROWING ROD SYSTEMS" dated 23 Apr. 2020.

FIELD

The present disclosure relates to medical implants. More particularly, the present disclosure relates to dynamic-seal-less self-actuating growing rod systems used as medical implants.

BACKGROUND

Hydraulics based self-actuating growing rod systems typically contain multiple static and dynamic sealing components in order to prevent leakage of the fluid contained therein to the external environment and also to maintain the pressure of the fluid at a pre-determined value.

Attributable to the constant motion thereof, having dynamic seal(s) in the growing rod systems is associated with some significant drawbacks such as wear and tear of the seal material resulting in debris creation and the consequent decrease in the system efficiency; leakage of the fluid in the body of the patient and the consequent infections and the like.

The inventors of the present disclosure have envisaged dynamic-seal-less self-actuating growing rod systems that mitigate the afore-mentioned drawbacks.

OBJECTS

It is an object of the present disclosure to provide a dynamic-seal-less self-actuating growing rod system.

It is yet another an object of the present disclosure to provide a dynamic-seal-less self-actuating growing rod system which is safe.

It is another object of the present disclosure to provide a dynamic-seal-less self-actuating growing rod system which is efficient.

It is still another an object of the present disclosure to provide a dynamic-seal-less self-actuating growing rod system which is economical.

It is a further object of the present disclosure to provide a dynamic-seal-less self-actuating growing rod system which is designed for long term use.

SUMMARY

The present disclosure provides a dynamic-seal-less self-actuating growing rod system (100) comprising at least one cylindrical static rod (2), at least one piston rod (6), coaxially coupled with said static rod (2) and configured to distract longitudinally out of the static rod (2); at least one fluid source (8) holding at least one sterile biocompatible fluid selected from the group consisting of water, deionized water, saline solution and any at least one gas selected from the group consisting of carbon dioxide, argon and nitrogen at a pre-determined pressure; at least one fluid transfer port (10) configured to transfer said sterile biocompatible fluid in said fluid source (8) to at least one fluid receptacle (12) at the same pre-determined pressure, wherein said at least one fluid receptacle (12) is in contact with said second piston end (6b) of said piston rod (6) at a first receptacle end (12a) and is connected to said fluid transfer port (10) at a second receptacle end (12b). The fluid receptacle (12) is at least one selected from the group consisting of metal bellows, polymeric bellows, polymeric balloon, polymeric tube and contains the said sterile biocompatible fluid, at said pre-determined pressure. The fluid receptacle (12) is made up of implant-grade polymeric material selected from the group consisting of polyethylene terephthalate, nylon, polyurethane and Pebax (polyether block amide) and the like. The metal bellows are made up at least one metal selected from the group consisting of titanium, nitinol, and stainless steel. The fluid receptacle (12) is characterized by being flexible, inflatable, collapsible, low profile to fit within the inner bore of the static rod (2) in a collapsed position and configured to withstand hoop stresses generated by the pressure of the fluid contained therein.

BRIEF DESCRIPTION OF THE ACCOMPANYING DRAWINGS

The present disclosure is illustrated in the accompanying non-limiting drawings, throughout which, reference letters indicate corresponding parts in the various figures.

Figure 5:
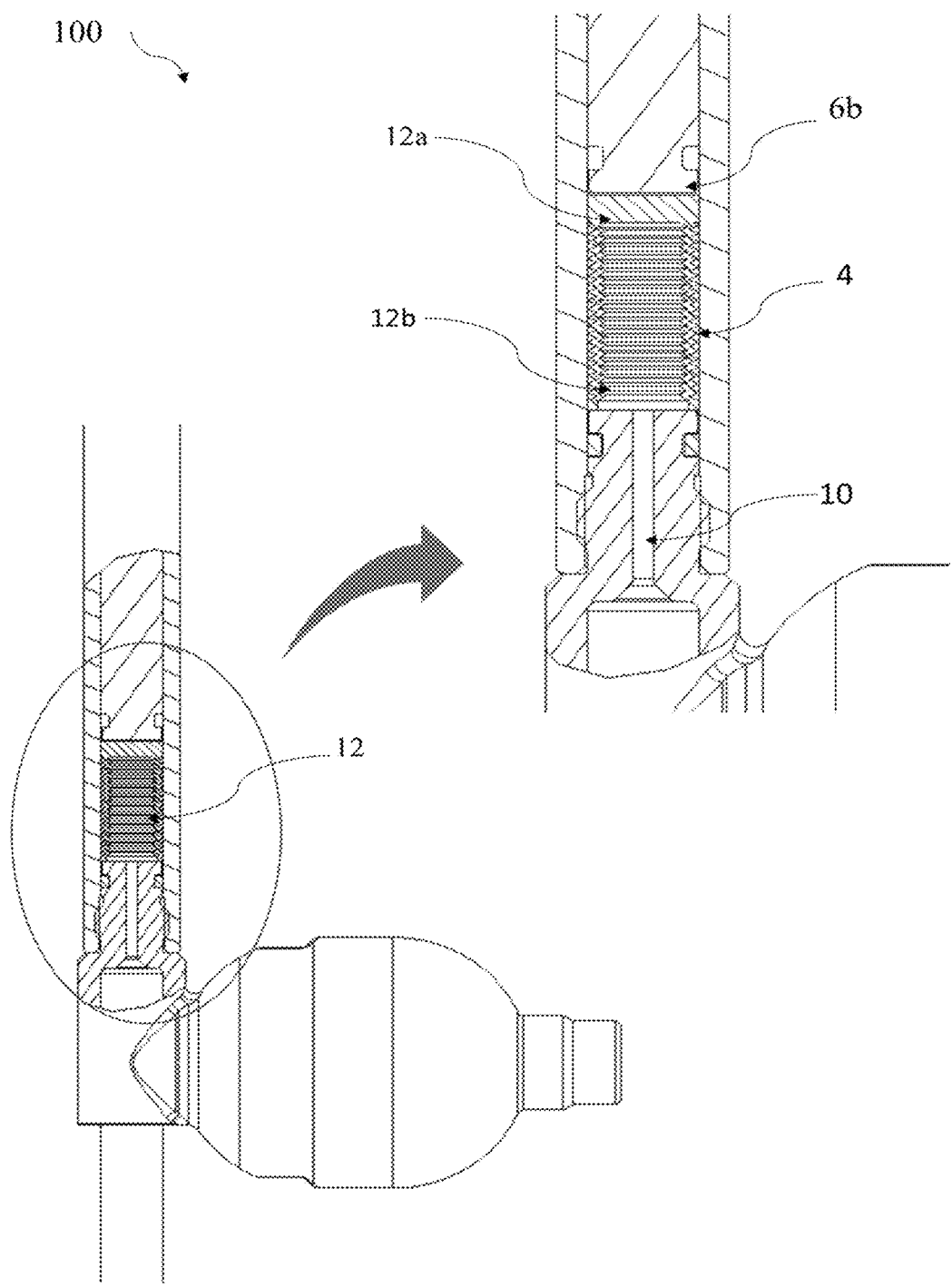
Figure 6:
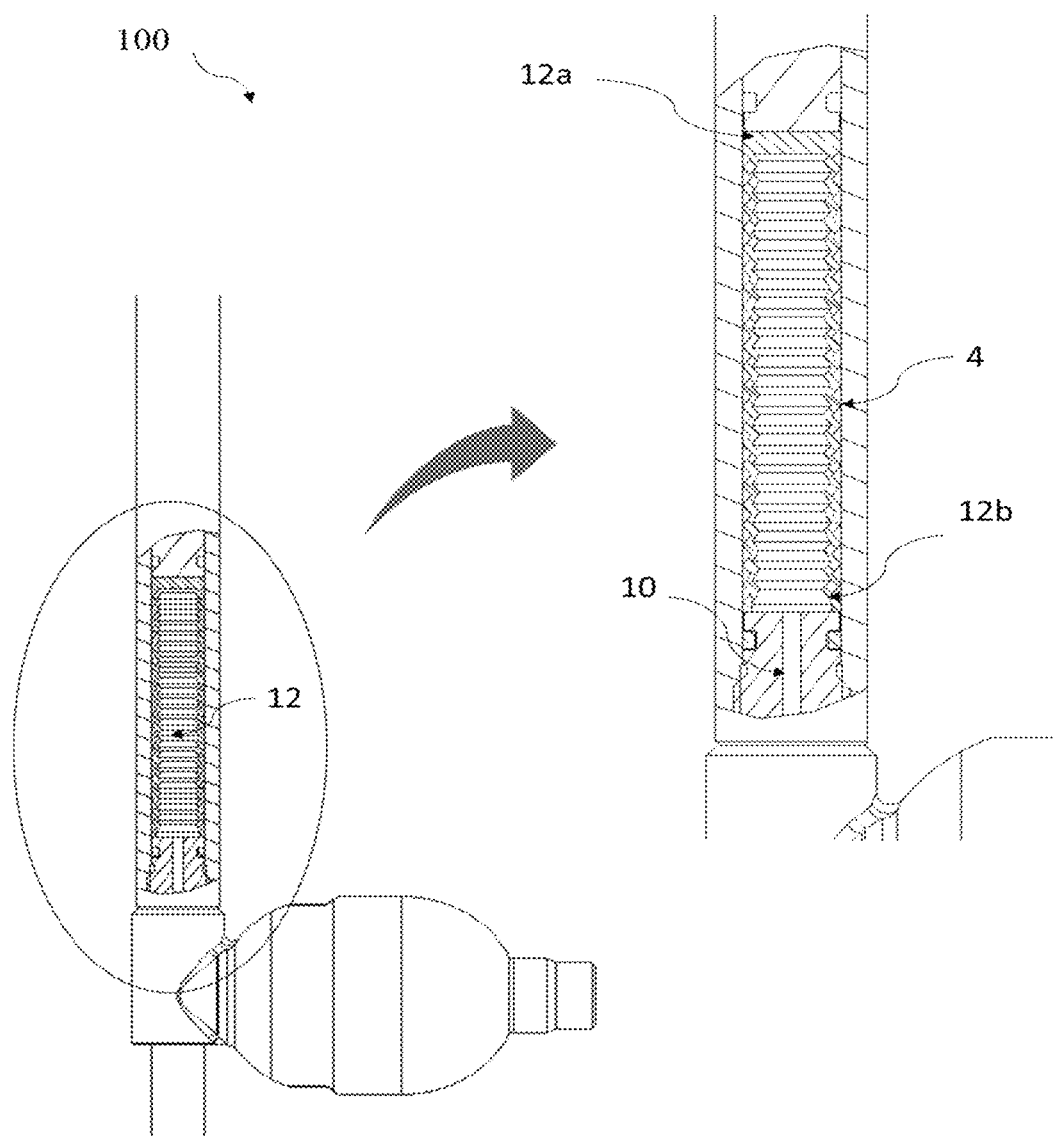
Figure 7:
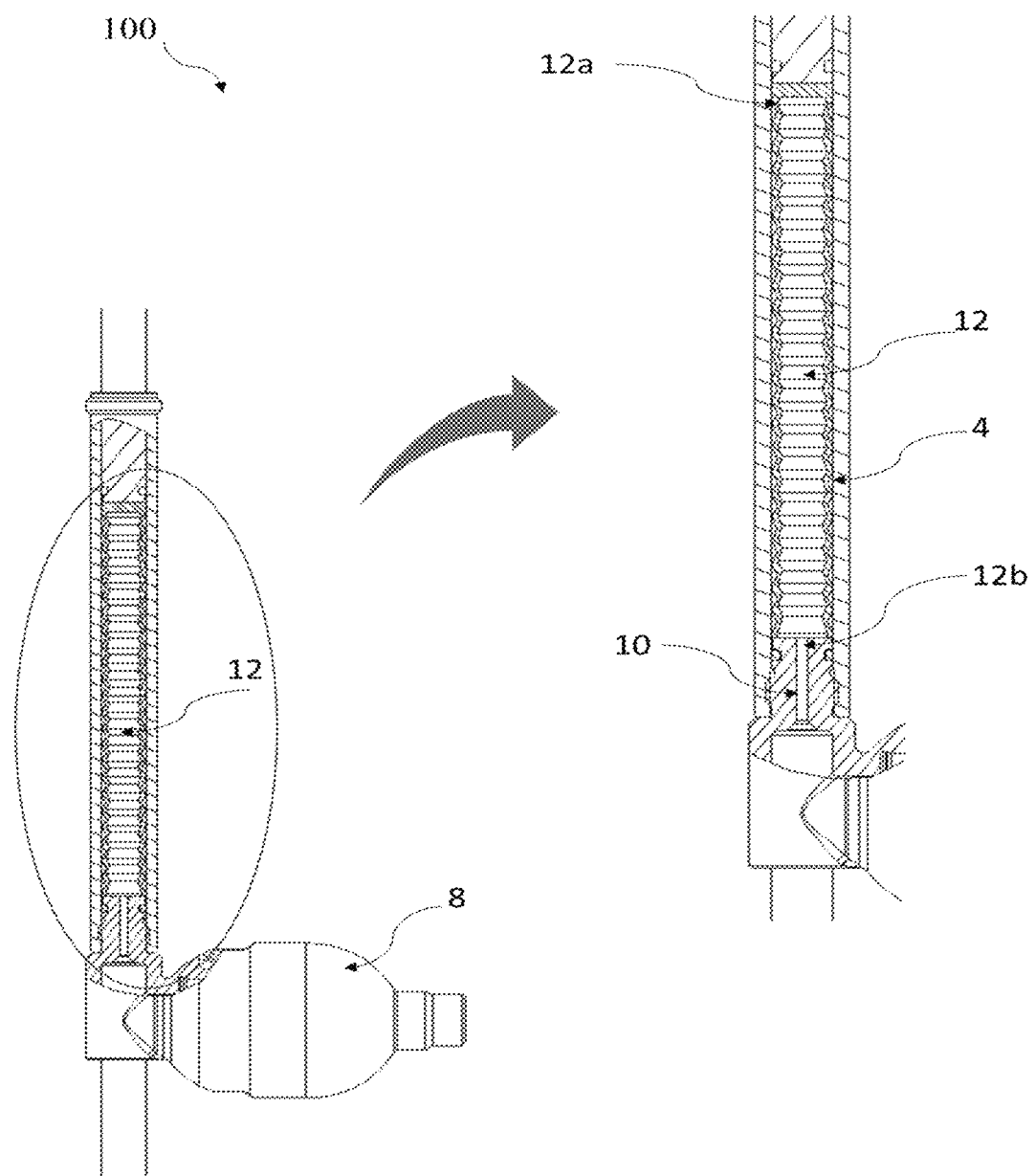
Figure 8:
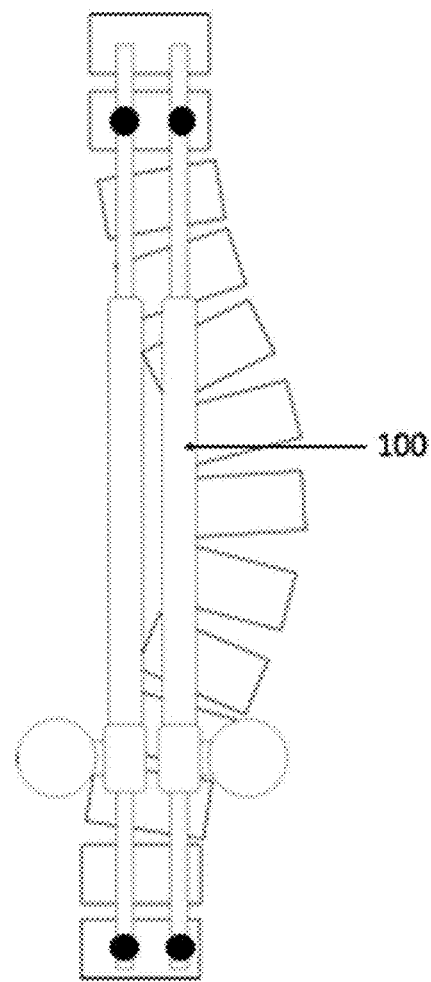

FIG. 5 illustrates a demonstration of the fluid receptacle (12) in a compressed position, FIG. 6 illustrates a demonstration of the fluid receptacle (12) intermediate position and FIG. 7 illustrates a demonstration of the fluid receptacle (12) fully expanded position; and FIG. 8 illustrates a demonstration of the dynamic-seal-less self-actuating growing rod system (100) of the present disclosure after implantation on the bony anatomy.

DESCRIPTION

Figure 1:
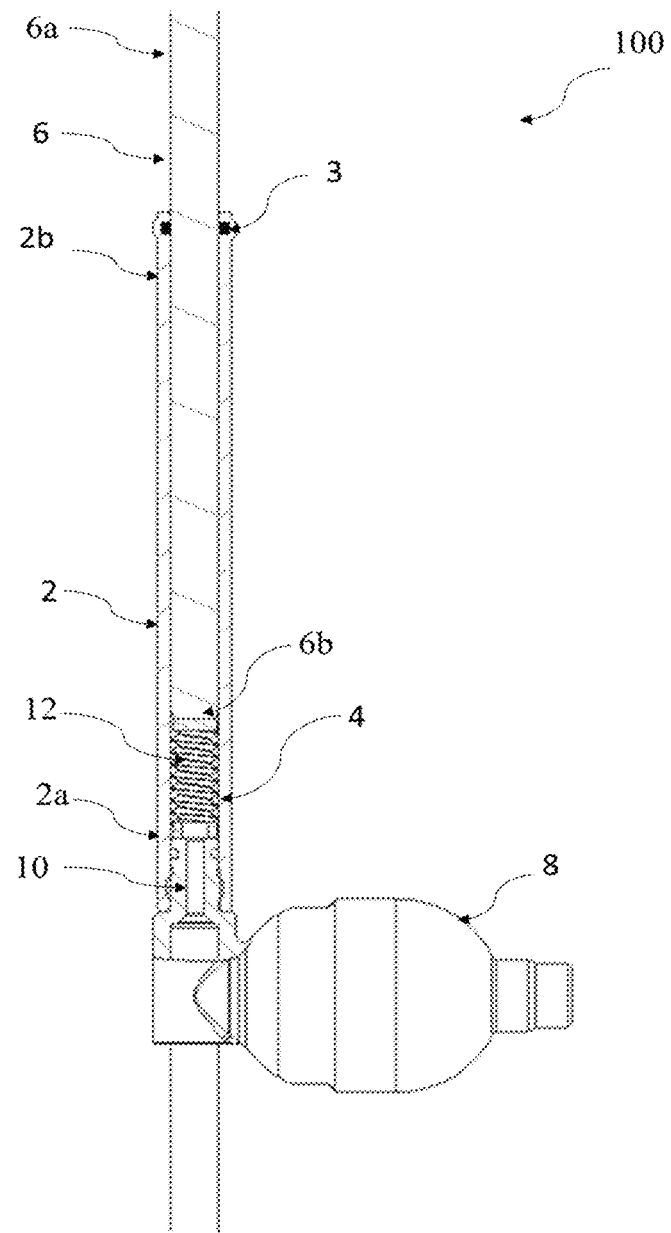
FIG. 1 illustrates an embodiment of the dynamic-seal-less self-actuating growing rod system (100) of the present disclosure.

The present disclosure relates to a dynamic-seal-less self-actuating growing rod system (100) comprising at least one cylindrical static rod (2), at least one piston rod (6), at least one fluid source (8), at least one fluid transfer port (10) and at least one fluid receptacle (12) as illustrated in FIG. 1. The dynamic-seal-less self-actuating growing rod system (100) is meant to be affixed across orthopedic deformities and applies correction force via at least one medium selected from the group that includes but is not limited to pressurized hydraulic or pneumatic fluid.

The static rod (2) of the present system (100) is hollow, assumes the form of a cylinder with an internal bore and comprises a first static end (2a) and a second static end (2b). The first static end (2a) is configured for fixation on to a deformed bony anatomy by means of at least one fixation element selected from the group consisting of screw(s), hook(s), band(s), wire(s), connector(s), plate(s), staple(s) or any other fixation element typically used in orthopedic surgery. The second static end (2b) is closed by at least one cap (3) which defines the area enclosed therein as a fluid receptacle shell (4). The cap (3) also facilitates the passing of the piston rod (6) there-through; whilst maintaining the position of the piston rod (6) with respect to the static rod (2). The static rod (2) hosts and provides support to the components housed therein.

The piston rod (6) of the present system (100) is coaxially coupled with the static rod (2) and is configured to distract longitudinally out of the static rod (2) in order to enable the growth of the bony anatomy. The first piston end (6a) of the piston rod (6) is configured for fixation on to a deformed bony anatomy by means of at least one fixation element selected from the group consisting of screw(s), hook(s), band(s), wire(s), connector(s), plate(s), staple(s) or any other fixation element typically used in orthopedic surgery. The second piston end (6b) of the piston rod (6) is disposed within the internal bore of the static rod (2) through the cap (3). The second piston end (6b) of the piston rod (6) in conventional systems comprises dynamic seals to prevent leakage of the fluid contained therein to the external environment. The present disclosure provides a system that obviates the inclusion of dynamic seals.

Figure 2:
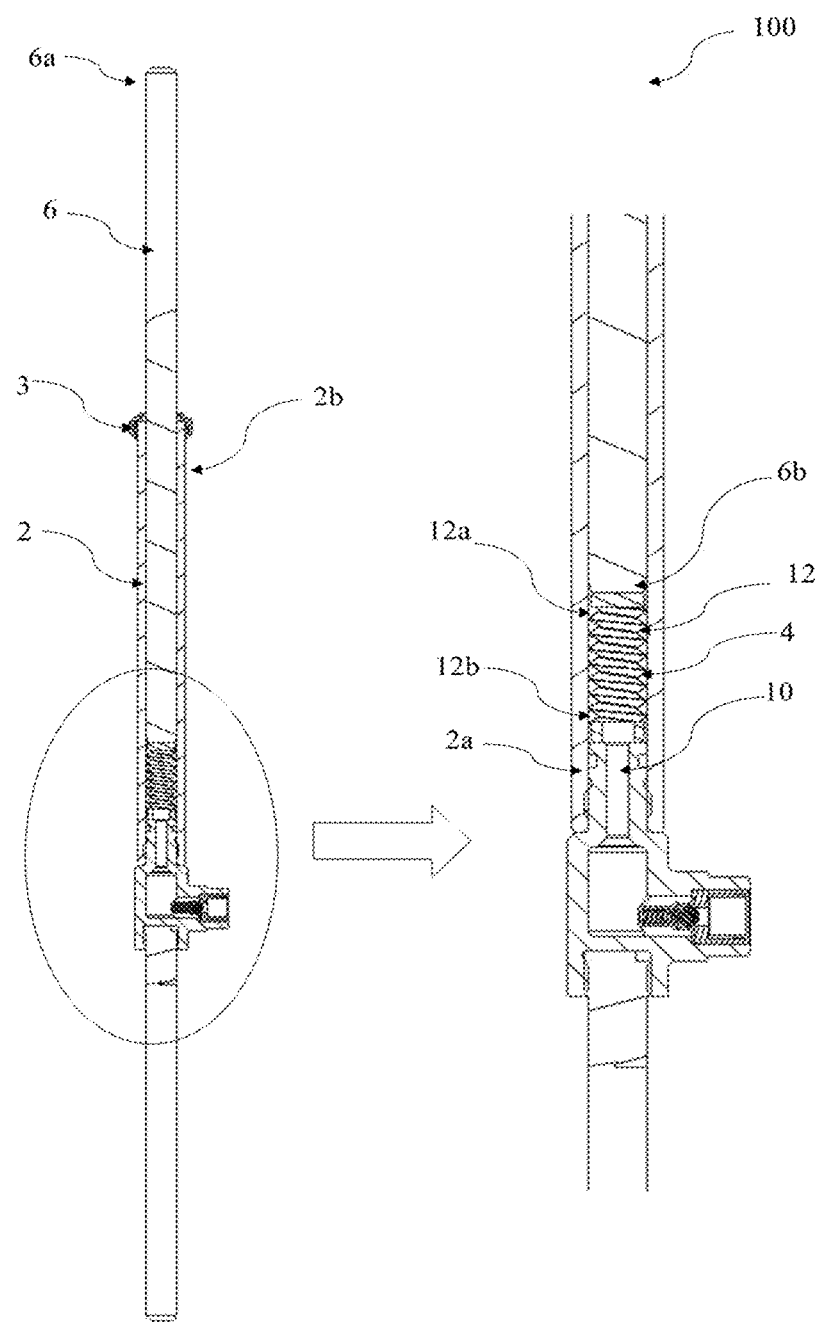
FIG. 2 illustrates another embodiment of the dynamic-seal-less self-actuating growing rod system (100) of the present disclosure.

The fluid source (8) holds at least one sterile biocompatible fluid selected from the group consisting of water, deionized water, saline solution and a gas at a pre-determined pressure. The gas is at least one selected from the group consisting of carbon dioxide, argon and nitrogen. The fluid source (8) is at least one selected from the group consisting of a permanently integrated pressure compensating device (FIG. 1) and a detachable pressure compensating device (illustrated in FIG. 2). In one embodiment, the permanently integrated pressure compensating device is an accumulator. In said embodiment, a minimally invasive surgery may be performed if the pressure inside the system needs to be increased. The detachable pressure compensating device is at least one selected from the group consisting of accumulators, fluid pumps, manual syringes, conventional vascular access ports or devices powered by electric motors or air compressors. The pressure compensating mechanism can be connected to the system (100) post implantation and stays connected to the system (100) during the operation cycle. If the pressure in the system (100) needs to be increased, the connected pressure compensating mechanism with the pressurized fluid is replaced by another one with the required rated pressure. In the embodiment where the fluid source is detachable, optionally, at least one non-return valve (NRV) is provided at the fluid transfer port (10) to ensure that the sterile biocompatible fluid is contained within the system (100) and doesn't leak out.

The fluid transfer port (10) of the present system (100) is configured to transfer the sterile biocompatible fluid contained in the fluid source (8) to at least one fluid receptacle (12). The fluid transfer port (10) ensures that the pre-determined pressure of the sterile biocompatible fluid contained in the fluid source (8) is maintained during the transfer.

The characterizing feature of the present system (100) is the at least one fluid receptacle (12) housed within the fluid receptacle shell (4). As the system (100) elongates, the fluid receptacle (12) expands to allow the fluid to fill the opened-up volume of the fluid receptacle (12). Once filled with the sterile biocompatible fluid at the pre-determined pressure, the fluid receptacle (12) presses onto the piston rod (6b) of the system to apply distraction force on the deformity.

The first receptacle end (12a) of the fluid receptacle (12) is in contact with the second piston end (6b) of the piston rod (6) and the second receptacle end (12b) of the fluid receptacle (12) is connected to the fluid transfer port (10). The fluid receptacle (12) is at least one selected from the group consisting of metal bellows, polymeric bellows, polymeric balloon and polymeric tube. The fluid receptacle (12) contains the sterile biocompatible fluid, at the pre-determined pressure of the fluid contained in the fluid source (8). The fluid receptacle (12) is made up of implant-grade polymeric material selected from the group consisting of polyethylene terephthalate, nylon, polyurethane and Pebax (polyether block amide) and the like. The metal bellows are at least one selected from the group consisting of titanium, nitinol, and stainless steel.

Figure 3:
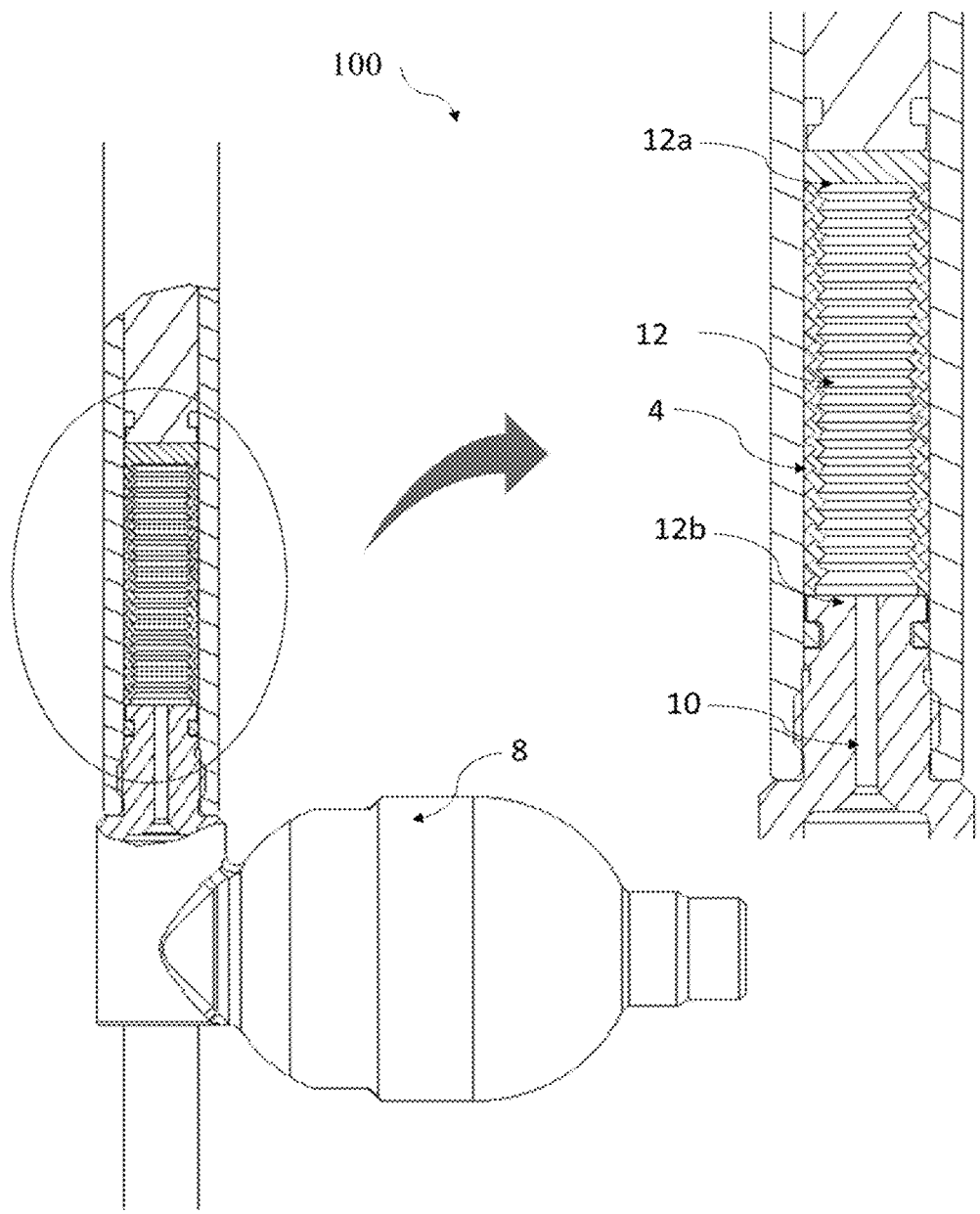
FIG. 3 illustrates yet another embodiment of the dynamic-seal-less self-actuating growing rod system (100) of the present disclosure.
Figure 4:
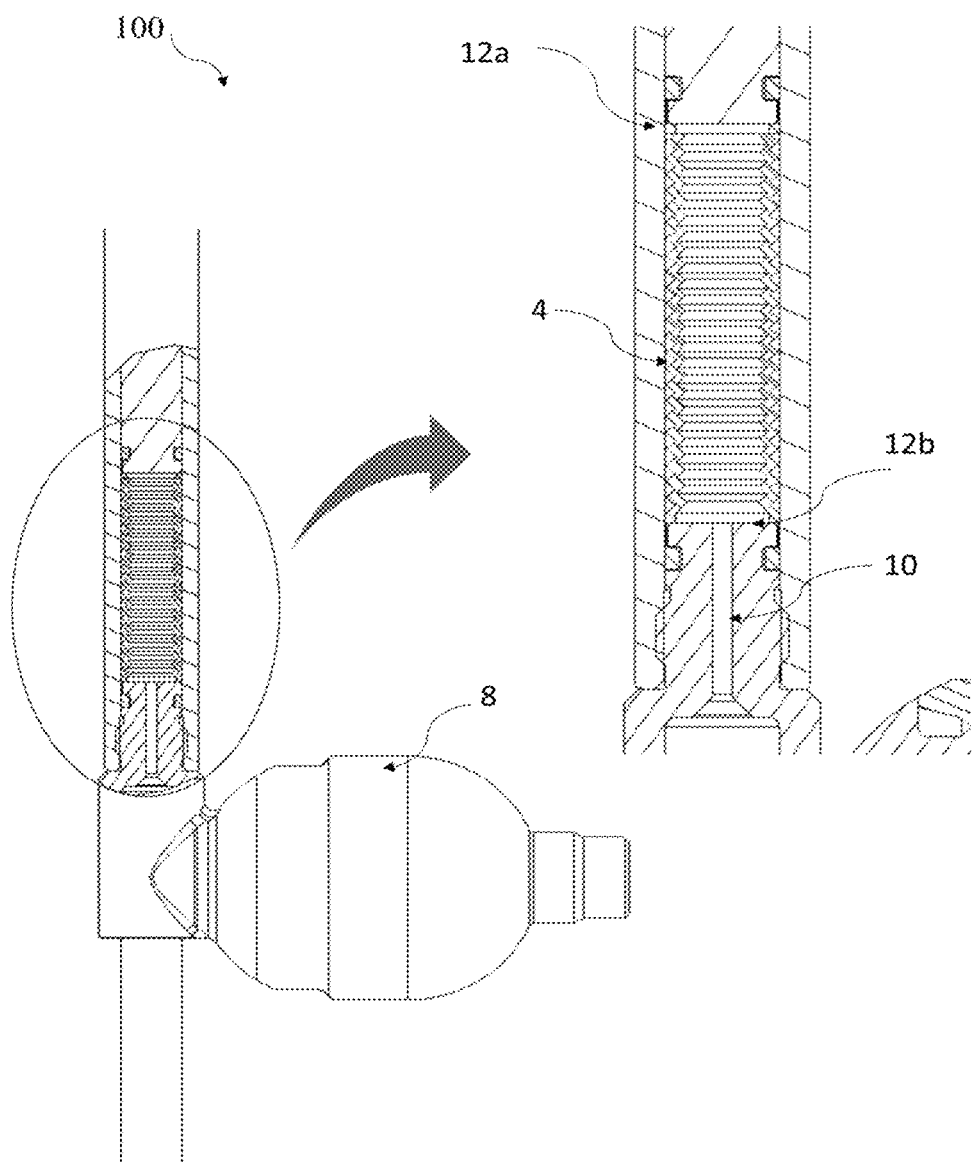
FIG. 4 illustrates still another embodiment of the dynamic-seal-less self-actuating growing rod system (100) of the present disclosure.

In one embodiment, the first receptacle end (12a) of the fluid receptacle (12) is closed (illustrated in FIG. 3). In another embodiment, the first receptacle end (12a) of the fluid receptacle (12) is open (illustrated in FIG. 4) and the sterile biocompatible fluid contained therein is in direct contact with the second piston end (6b) of said piston rod (6). The open first receptacle end (12a) of the fluid receptacle (12) is affixed to the second piston end (6b) of said piston rod (6) by at least one means selected from the group consisting of mechanical constraints, welding and adhesives. In the embodiment where the fluid receptacle (12) is open, the expansion of the fluid receptacle is through the distraction of the piston rod facilitated through combined force of fluid pressure inside the fluid receptacle and the natural growth of the bony anatomy. In the embodiment where the fluid receptacle (12) is closed, the expansion of the fluid receptacle is through fluid pressure inside the fluid receptacle only.

The fluid receptacle (12) is characterized by being flexible, inflatable, collapsible, low profile to fit within the inner bore of the static rod (2) in a collapsed position and configured to withstand hoop stresses generated by the pressure of the fluid contained therein. The shape of the fluid receptacle (12) can vary on the basis of the application. The fluid receptacle shell (4) ensures a single axis movement of the fluid receptacle (12).

When the sterile biocompatible fluid enters the fluid receptacle (12), the receptacle (12) begins to elongate within the cavity of the static rod (2). The rigid support of the cylinder cavity ensures that the elongation is linear. The piston end of the piston rod (6) thus travels within the static rod (2) outwards. When the system (100) distracts upon the elongation of the fluid receptacle (12), a distraction force acts on the bony anatomy to which it is anchored. In self-actuating bony anatomy growth-driven applications, the elongation is quasistatic. In displacement-driven applications the elongation may be ramped and in pressure driven applications, the elongation may be stepped.

Typical growing rod systems contain a plurality of static and dynamic seals to prevent leakage of the sterile biocompatible fluid contained in the system (100) to the external environment. In conventional growing rod systems, a seal is present on the piston rod (6) which is in constant contact with the wall of the static rod (2). The seal is subjected to the pressure of the fluid inside the fluid reservoir. Also, due to constant movement and friction, there is a possibility of leakage of the hydraulic fluid around this seal. The system (100) of the present disclosure comprises at least one cap (3) for the above-mentioned purpose; however, does not contain any dynamic seal(s) as the sterile biocompatible fluid is contained in the leak-proof inflatable, flexible receptacle (12). Hence, the piston rod (6) does not need a dynamic seal. Since the fluid is trapped inside the fluid receptacle (12), chances of leakage past the rod are highly reduced. Any leakage from the system results in pressure drop and thus a reduction in the distraction force. Hence, prevention of leakage of the fluid is a crucial advantage of the present system (100). Further, significant drawbacks such as wear debris generated from the seals are obviated. The present system (100) is, therefore, referred to as dynamic-seal-less and has enhanced efficiency and safety.

The afore-stated components of the system (100) of the present disclosure are manufactured from biocompatible materials. Further, the components of the system (100) of the present disclosure are manufactured from at least one material selected from the group that includes but is not limited to metal(s), metal alloys and polymers. For the purpose of the present disclosure, the term metal is at least one selected from the group that includes but is not limited to titanium, cobalt-chromium-molybdenum, and stainless steel or any other metal or metal alloy suitable from biocompatibility and strength perspective. For the purpose of the present disclosure, the term polymers is at least one selected from the group that includes but is not limited to high density polyethylene (HDPE), polyurethane, polycarbonate urethane, ultra-high molecular weight polyethylene (UHMWPE), polyethylene terephthalate (PET), polyether ether ketone (PEEK) and silicone or any other polymer suitable from biocompatibility and strength perspective. All the components of the system (100) of the present disclosure may be fabricated separately and attached together using conventional manufacturing techniques. The length and diameter of the static rod (2) may vary based on the application it is used in.

The embodiments described herein above are non-limiting. The foregoing descriptive matter is to be interpreted merely as an illustration of the concept of the present disclosure and it is in no way to be construed as a limitation. Description of terminologies, concepts and processes known to persons acquainted with technology has been avoided for the sake of brevity.

TECHNICAL ADVANTAGES AND ECONOMIC SIGNIFICANCE

The technical advantages and economic significance of the present system (100) of the present disclosure include but are not limited to:

Absence of dynamic seal;
Leak-proof;
Reduced debris generation;
Enhanced safety; and
Enhanced efficiency.

We claim:

1. A dynamic-seal-less self-actuating growing rod system comprising:
   a. at least one cylindrical static rod with an internal bore comprising a first static end and a second static end, wherein said second static end is sealed by at least one cap to define the area enclosed therein as a fluid receptacle shell;
   b. at least one piston rod, coaxially coupled with said static rod and comprising a first piston end and a second piston end; wherein said second piston end is disposed within the internal bore of said static rod through said cap and is configured to distract longitudinally out of the static rod;
   c. at least one fluid source holding at least one sterile biocompatible fluid at a pre-determined pressure; and
   d. at least one fluid transfer port configured to transfer said sterile biocompatible fluid in said fluid source to at least one fluid receptacle at the same pre-determined pressure,
      wherein said at least one fluid receptacle is housed within said fluid receptacle shell and is in contact with said second piston end of said piston rod at a first receptacle end and is connected to said fluid transfer port at a second receptacle end,
      wherein said at least one fluid receptacle being at least one selected from the group consisting of metal bellows, polymeric bellows, polymeric balloon, and polymeric tube and contains the said sterile biocompatible fluid at said pre-determined pressure.

2. The system as claimed in claim 1, wherein the first receptacle end of the fluid receptacle is closed and the expansion of the fluid receptacle is through fluid pressure inside the fluid receptacle only.

3. The system as claimed in claim 1, wherein the first receptacle end of the fluid receptacle is open and the expansion of the fluid receptacle is through the distraction of the piston rod facilitated through combined force of fluid pressure inside the fluid receptacle and the natural growth of the bony anatomy.

4. The system as claimed in claim 1, wherein said fluid receptacle is flexible, inflatable, collapsible, low profile to fit within the inner bore of the static rod in a collapsed position, and is configured to withstand hoop stresses generated by the pressure of the fluid contained therein.

5. The system as claimed in claim 1, wherein said fluid receptacle is made up of implant-grade polymeric material selected from the group consisting of polyethylene terephthalate, nylon, polyurethane and Pebax and the like.

6. The system as claimed in claim 1, wherein the shape of said fluid receptacle can vary on the basis of the application.

7. The system as claimed in claim 1, wherein the fluid receptacle shell ensures a single axis movement of the fluid receptacle.

8. The system as claimed in claim 1, wherein said fluid source is at least one selected from the group consisting of a permanently integrated pressure compensating device and a detachable pressure compensating device.

9. The system as claimed in claim 1, wherein said sterile biocompatible fluid is at least one selected from the group consisting of water, deionized water, saline solution and gas, wherein said gas is at least one selected from the group consisting of carbon dioxide, argon and nitrogen.

10. The system as claimed in claim 1, wherein said fluid transfer port is accompanied by at least one non-return check valve.

11. The system as claimed in claim 1, wherein said first static end of said static rod and said first piston end of said piston rod are configured for fixation on to a deformed bony anatomy by means of at least one fixation element selected from the group consisting of screw(s), hook(s), band(s), wire(s), connector(s), plate(s), staple(s) and any other fixation element used in orthopedic surgery.

12. The system as claimed in claim 1, wherein the components are manufactured from biocompatible materials.

* * * * *